US006352826B1

(12) United States Patent
Jehuda-Cohen

(10) Patent No.: US 6,352,826 B1
(45) Date of Patent: *Mar. 5, 2002

(54) METHOD AND KIT FOR THE DETECTION OF RETROVIRAL SPECIFIC ANTIBODIES IN SERONEGATIVE INDIVIDUALS

(75) Inventor: Tamar Jehuda-Cohen, Rehovot (IL)

(73) Assignee: Yoreh Biotechnologies, Ltd., Moshav Gimzo (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/855,371

(22) Filed: May 13, 1997

Related U.S. Application Data

(63) Continuation-in-part of application No. 08/275,933, filed on Jul. 15, 1994, now Pat. No. 5,637,453, which is a continuation of application No. 08/095,824, filed on Jul. 21, 1993, now abandoned, which is a continuation of application No. 07/797,730, filed on Nov. 25, 1991, now abandoned.

(51) Int. Cl.$^7$ ................................................ C12Q 1/70
(52) U.S. Cl. ............................. 435/5; 435/7.1; 422/61
(58) Field of Search ........................... 435/5, 7.1, 7.2, 435/7.9, 172.3

(56) References Cited

U.S. PATENT DOCUMENTS

| | | | |
|---|---|---|---|
| 5,156,949 A | * 10/1992 | Luciw et al. | ................... 435/5 |
| 5,637,453 A | * 6/1997 | Jehuda-Cohen | ................ 435/5 |

FOREIGN PATENT DOCUMENTS

| | | |
|---|---|---|
| DE | 195 15 219 A | 10/1996 |
| EP | 0203 403 A | 12/1986 |
| WO | WO93 11435 A | 6/1993 |
| WO | WO 93 14189 A | 7/1993 |

OTHER PUBLICATIONS

Stites et al., Basic and Clinical Immunology, Sixth Edition, Appleton & Lange, Norwalk, p. 295, 1987.*

Doldi et al., "Proliferation and Interferon Production in Whole Blood Samples and Isolated Lymphocyte Preparations," J. Interferon Res. 5:55–64, 1985.*

Jehuda–Cohen et al., "Polyclonal B–cell Activation Reveals Antibodies Against Human Immunodeficiency Virus Type 1 (HIV–1) in HIV–1–seronegative individuals," Proc. Natl. Acad. Sci. USA 87:3972–3976, 1990.*

(1) Jehuda–Cohen, et al., "Polyclonal B–cell activation reveals antibodies against human immunodeficiency virus type 1 (HIV–1) in HIV–1–seronegative individuals", Proc. Natl. Acad. Sci. USA, Immunology, vol. 87, pp. 3972–3976 (May 1990).

(2) Technical Bulletin published by DuPont: "Human Immunodeficiency Virus Type–1 (HIV–1) Biotech/DuPont HIV–1 Western Blot Kit".

(3) Technical Bulletin published by Abbott Laboratories: Human Immunodeficiency Virus Type 1 Abbott HIV–1 EIA, "Enzyme Immunoassay for the Detection of Antibody to Human Immunodeficiency Virus Type 1 (HIV–1) in Human Serum or Plasma", Abbott Laboratories Diagnostic Division, Customer Support Center (USA), Publication No. 83–4689/R2 (1989).

(4) Hofmann, et al., "Lymphocyte transformation response to pokeweed mitogen as a predictive marker for development of AIDS and AIDS related symptom in homosexual men with HIV antibodies", British Medical Journal, Vo. 295, pp. 293–295 (Aug. 1, 1987).

(5) Loche, et al., "Identification of HIV–infected seronegative individuals by a direct diagnostic test based on hybridisation to amplified viral DNA", The Lancet, pp. 418–421 (Aug. 20, 1988).

(6) Ou, et al., "DNA Amplification for Direct Detection of HIV–1 in DNA of Peripheral Blood Mononuclear Cells", Science Reports, Vo. 239, pp. 295–297 (Jan. 15, 1988).

(7) Saito, et al., "Detection of HTLV–1 Genome in Seronegative Infants Born to HTLV–1 Seropositive Mothers by Polymerase Chain Reaction", Jpn. J. Cancer Res., vol. 80, pp. 808–812 (Sep. 1989).

(List continued on next page.)

Primary Examiner—Laurie Scheiner
Assistant Examiner—Jeffrey S. Parkin
(74) Attorney, Agent, or Firm—Eitan, Pearl, Latzer & Cohen-Zedek

(57) ABSTRACT

Serological detection of antibodies against a variety of infectious disease agents is considered as evidence of exposure and/or active infection. Notably, serological screening techniques are being utilized for the detection of various retroviruses, including the human immunodeficiency virus type 1 (HIV-1). Current serological techniques, however, do not identify clinically asymptomatic individuals who are infected but lack detectable levels of retroviral-reactive antibodies. The present invention is directed toward an improved method and kit for detecting retroviral-specific antibodies in the whole blood of individuals who test seronegative by conventional assay techniques. The assay format utilizes a mitogen to induce retroviral-specific antibody production in a whole blood sample. This format provides a rapid and facile means for detecting retroviral infection in patients prior to seroconversion.

14 Claims, No Drawings

OTHER PUBLICATIONS (8) Steckelberg, et al., "Subsepecialty Clinics" Infectious Diseases—Seronegative Testing for Human Immunodeficiency Virus Antibodies, *Mayo Clin. Proc.,* vol. 63, p. 373–380 (1988).

(9) Stramer, et al., "Markers of HIV Infection Prior to IgG Antibody Seropositivity", JAMA, Clinical Investigation, vol. 262, No. 1, pp. 64–69 (Jul. 7, 1989).

(10) Hofmann, et al., "HIV–Induced Immunodeficiency—Relatively Preserved Phytohemagglutinin as Opposed to Decreased Pokeweed Mitogen Response May be Due to Possibly Preserved Responses Via CD2 Phytohemagglutinin Pathway", *J. Immunol.,* vol. 142, No. 6, pp. 1874–1880 (Mar. 15, 1989).

(11) Serk, et al., "Lymphocyte activation by phytohemagglutinin and pokeweed mitogen—identification of proliferating cells by monoclonal antibodies", *Journal of Immunological Methods,* vol. 99, pp. 167–172 (1987).

(12) Amadori, et al., "HIV–1 Specific B Cell Activation—A Major Constituent of Spontaneous B Cell Activation during HIV–1 Infection", *The Journal of Immunology,* vol. 143, No. 7, pp. 2146–2152 (Oct. 1, 1989).

(13) Rosenkoetter, et al., "T Cell Regulation of Polyclonally Induced Immunoglobulin Secretion in Humans", *The Journal of Immunology,* vol. 132, No. 4, pp. 1779–1783 (Apr. 1984).

(14) Levinson, et al., "In vitro IgM rheumatoid–factor production induced by tetanus toxoid", *J. alergy Clin. Immunol.,* pp. 730–736 (Apr. 1988).

(15) Karsh, et al., "In vitro IgM and IgM rheumatoid factor production in response to *Staphylococcus aureus* Cowan I and pokeweed mitogen: the contribution of $CD5^+$(Leu 1) B cells", *Clin. Exp. Immunol.,* vol. 77, pp. 179–183 (1989).

(16) Schnittman, et al., "Direct Polyclonal Activation of Human B. Lymphocytes by the Acquired Immune Deficiency Syndrome Virus", *Science Reports,* vol. 233, pp. 1084–1086 (Sep. 5, 1986).

(17) Koenig, et al., "Detection of AIDS Virus in Macrophage in Brain Tissue from AIDS Patients with Encephalopathy", *Science Reports,* vol. 233, pp. 1089–1093 (Sep. 5, 1986).

(18) Wopsy, et al., "Isolation of AIDS Associated Retrovirus from Genital Secretions of Women with Antibodies to the Virus", *The Lancet,* pp. 527–529 (Mar. 8, 1996).

(19) Gartner, et al., "The Role of Mononuclear Phagocytes in HTLV–III/LAV Infection", *Science Reports,* vol. 233, pp. 215–219 (Jul. 11, 1986).

(20) Young, John A.T., "HIV and HLA similarity", *Nature,* vol. 333, p. 215 (May 1988).

(21) Samter, et al., "Immunological Diseases—Fourth Edition", *Little, Brown and Company,* vol. 1, pp. 445–447; pp. 580–582; and p. 913 (1988).

(22) Andiman, Warren A., "Virologic and Serologic Aspects of Human Immunodeficiency Virus Infection in Infants and Children" *Seminars in Perinatology,* vol. 13, No. 1, pp. 16–26 (Feb. 1989).

(23) Edelman, et al., "AIDS: a syndrome of immune dysregulation, dysfunction, and deficiency", *The FASEB Journal,* vol. 3, pp. 22–30 (Jan. 1989).

(24) Dorsen, et al. "Anti–Lymphocyte Antibodies in Patients with the Acquired Immune Deficiency Syndrome", *The American Journal of Medicine,* vol. 78, pp. 621–626 (Apr. 1985).

(25) Kopelman, et al., "Association of Human Immunodeficiency Virus Infection and Autoimmune Phenomena", *The American Journal of Medicine,* vol. 84, pp. 82–88 (Jan. 1988).

(26) Lerche, et al., "Inapparent Carriers of Simian Acquired Immune Deficiency Syndrome Type D Retrovirus and Disease Transmission with Saliva", *INCI,* vol. 77, No. 2, pp. 489–495 (Aug. 2, 1986).

(27) Golding, et al., "Identification of Homologous Regions in Human Immunodeficiency Virus Igp41 and Human MHC Class II β 1 Domain", *Journal of Experimental Medicine,* vol. 167, pp. 914–923 (Mar. 1988).

(28) Imagaway, et al. "Human Immunodeficiency Virus Type 1 Infection in Homosexual Men Who Remain Seronegative for Prolonged Periods", *The New England Journal of Medicine,* vol. 320, No. 22, pp. 1458–1462 (Jun. 1, 1989).

(29) Wolinsky, et al., "Human Immunodeficiency Virus Type 1 (HIV–1) Infection a Median of 18 Months before a Diagnostic Western Blot", *American College of Physicians—Annals of Internal Medicine,* vol. 111, No. 12, pp. 961–972 (Dec. 15, 1989).

(30) Amadori et al., "In–Vitro Production of HIV–Specific Antibody in Children at Risk of AIDS", *The Lancet,* pp. 852–854 (Apr. 16, 1988).

(31) Pahwah, et al., "Influence of the human T–lymphotropic virus–lymphadenopathy–associated virus on functions of human lymphocytes: Evidence for immunosuppressive effects and polyclonal B–cell activation by banded viral preparations", *Proc. Natl. Acad. Sci. USA,* vol. 82, pp. 8198–8202 (Dec. 1988).

(32) Weimer, et al., "B Lymphocyte Response as an Indicator of Acute Renal Transplant Rejection", *Transplantation,* vol. 48, No. 4, pp. 572–575 (Oct. 1989).

(33) Primi, et al., "Sera from Lipopolysaccharide (LPS)–Injected Mice Exhibit Comoplement–Dependant Cytotoxicity against Syngeneic and Autologous Spleen Cells", *Cellular Immunology,* vol. 32, pp. 252–262 (1977).

(34) Thomas, et al, "Functional Analysis of Human T Cell Subsets Defined by Monoclonal Antibodies", *J. Immunol.,* vol. 125, No. 6, pp. 2402–2407 (Dec. 1980).

(35) Stevens, et al., "Regulation of antibody isotype secretion by subsets of antigen–specific helper T cells", *Nature,* vol. 334, pp. 255–258 (Jul. 21, 1988).

(36) Yamauchi, et al. "Suppression of Hepatitis B antibody Synthesis by Factor Made by T Cells from Chronic Hepatitis B Carriers", *The Lancet,* pp. 324–326 (Feb. 13, 1988).

(37) Siekovits et al., *Science,* vol. 238, pp. 1575–1578 (1987).

(38) Israel et al., *J. Immunology,* vol. 143(12) pp. 3956–3960 (1989).

(39) R. Yarchoan, "Mechanisms of B Cell Activation in Patients with Acquired Immunodeficiency Syndrome and Related Disorders", *Journal of Clinical Investigation,* vol. 78, pp. 439–447 (1986).

(40) M. Leroux, "A Whole–Blood Lymphoproliferation Assay For Measuring Cellular Immunity Against Herpes Viruses" *J. Immunol. Methods,* vol. 79, pp. 215–262 (1985).

(41) Böhnlein et al., *Cell,* vol. 53, pp. 827–836, (1988).

(43) Cole et al., *Abstract Int. Conf. Ans. Jul.,* Ab#PoC4216.

(44) Chowhurdy et al., *Virology,* vol. 176, pp. 126–132 (1990).

(45) R.H. Zubler et al., "Frequencies of HIV–reactive B–cells in sepopositive and seronegative individuals" *Clin. Exp. Immuno.,* vol. 87, pp. 31–36 (Jun. 1992).

(46) Hall and Gordon, "Reproducibility, efficacy, and methodology of mitogen–induced lymphocyte transformations by the whole blood assay", *J. Immunol. Methods.,* vol. 12, pp. 31–38 (1976).

(47) Strongin, W. "Sensitivity, Specificity, and Predictive Value of Diagnostic Tests: Definitions and Clinical Appli cations", in Laboratory Diagnosis of Viral Infections, Lennette, E., ed., Marcel Dekker, Inc., New York, pp. 211–219 (1993).

(48) DeFranco, A. "B Lymphocyte Activation" in Fundamental Immunology, Paul, ed., Raven Press, Ltd., New York p. 525 (1993).

* cited by examiner

METHOD AND KIT FOR THE DETECTION OF RETROVIRAL SPECIFIC ANTIBODIES IN SERONEGATIVE INDIVIDUALS

This application is a continuation-in-part application of U.S. Ser. No. 08/275,933 filed Jul. 15, 1994, now U.S. Pat. No. 5,637,453, issued Jun. 10, 1997, which is a continuation of U.S. Ser. No. 08/095,824, filed Jul. 21, 1993, now abandoned, which is a continuation of U.S. Ser. No. 07/797,730, filed Nov. 25, 1991 now abandoned.

TECHNICAL FIELD

The present invention relates to an improved method and kit for detecting antibodies in whole blood of individuals who test seronegative by conventional assay techniques. More particularly, the present invention relates to an assay for detecting possible retrovirus infection, such as infection by the HIV virus, which utilizes a mitogen in whole blood to stimulate antibody production by peripheral blood mononuclear cells. The present invention also relates to an improved assay kit which does not require the separation of peripheral blood mononuclear cells from whole blood prior to culture with pokeweed mitogen.

BACKGROUND OF THE INVENTION

As used herein, mitogen means any substance capable of activating B-cells and/or T-cells. The term "whole blood" means blood collected with heparin, EDTA, or any other substance that prevents coagulation and clotting. The term whole blood as used herein also includes blood collected from and animal or human with heparin, ethylenediaminetetraacetate, or any other substance that prevents coagulation and clotting. "Whole blood" can also mean blood wherein the red blood cells have been lysed while maintaining the viability of the remaining white blood cells.

Serological detection of antibodies against a variety of infectious disease agents is considered evidence of exposure to and/or active infection by the agent. Serological detection of antibodies could also be useful for early detection of cancer and for predicting the success of organ or tissue transplants. Enzyme-linked immunosorbent assay (ELISA) commercial kits are commonly used as screening tests for serological detection of antibodies. The western blot technique has been the method most widely used to confirm ELISA-reactive serum samples, although other methods such as immunofluorescence, may also be applicable. Polymerase chain reaction (PCR) technique may also be used to confirm results of a preliminary assay.

As part of standard ELUSA procedure, test serum is incubated with specific antigens that are immobilized on beads or wells. Non-specific antibody in the serum is removed by washing, but the antibodies with affinity for the antigens present in the system remain bound. When the appropriate developing reagents are added, spectrophotometrically detectable color is produced, the optical density of which is proportional to the amount of antibodies bound. The standard optical density is established by the manufacturer of the ELISA kit and affects both the sensitivity and specificity of the assay. Generally, a sample that is positive is retested twice and deemed "positive" only if at least one of the subsequent two tests is also reactive. Due to its subjective nature, the prediction value of a positive ELISA varies depending on the degree of ELISA reactivity and the probability of infection. Additionally, results may be affected by the presence of a variety of other conditions, including autoimmune disease.

Western blot technique is widely used to confirm ELISA-reactive serum samples. In the Western blot test, the desired antigens are electrophoretically separated into discrete bands that are then transferred onto nitrocellulose paper. Particular antigens will exhibit identifiable and characteristic banding patterns. The nitrocellulose test strips are then incubated with donor serum specimens. Antibodies present in the sample will bind with specific antigenic bands and thus facilitate separation and identification of the antibodies present. Prepared nitrocellulose test strips are commercially available for a variety of tests. The Western blot technique is considered more specific than the ELISA technique, yet it is usually less sensitive.

Current serological techniques, however, do not identify individuals who are infected but lack detectable levels of reactive antibodies. Examples of conditions in which detectable levels of reactive antibodies are lacking include autoimmune diseases, where antibody may be present only a portion of the time and suppressed the remainder of the time or where antibodies are bound to the antigen forming immune complexes and thus may be nondetectable in serum; some forms of cancer, where antibody production against the tumor may be suppressed by some specific process in the development of the cancer, organ and tissue transplants, where the recipient is not producing antibodies against the potential donor but would suffer rapid graft rejection because of recall stimulation of the immune system due to a cross-reaction of the donor's antigens with antigens the recipient was previously exposed to; cytomegalovirus, which causes a reduction in antibody production; and, a host of other infections in which antibody production is subsequently suppressed. A variety of viruses can interfere with immunological functions as well. The inhibition that is induced may be specifically related to immune reactions to the virus or may be non-specific and affect many components of the general immune system of the host.

For example, recently a new class of human retroviruses which infect a subset of lymphocytes has been shown to cause profound immunological suppression and to cause an individual who has been infected with the virus to develop susceptibility to many pathogenic organism. Human Immunodeficiency Virus (HIV) infects T-lymphocytes belonging to the helper cell subset. The infection and subsequent loss of T-helper cells is thought to lead to immunosuppression and the resulting acquired inmmunodeficiency syndrome (AIDS).

AIDS was first reported by the Center for Disease Control (CDC) in 1981. Individuals were defined as having AIDS if the following conditions were present: (1) a reliably diagnosed disease such as *P.Carinii* pneumonia, other opportunistic infection, or Kaposi's sarcoma in a person less than 60 years of age that suggested an underlying cellular immune defect, and (2) occurrence of the disease in the absence of a cellular immune deficiency that could be ascribed to another factor (Samter, M., ed. "Immunological Diseases", 4th ed, p. 445 (1988)). Two related disorders were also noted which manifested a variety of signs and symptoms suggestive of AIDS but did not meet the criteria established by the CDC. These syndromes are described by the terms AIDS-related complex (ARC) and chronic lymphadenopathy. ARC is characterized by fatigue, fever, night sweats, diarrhea, unintentional weight loss, oral candidiasis, generalized lymphadenopathy, leukopenia, and anemia, accompanied by immunological abnormalities similar to AIDS. Chronic lymphoadenapathy syndrome describes a condition of chronic lymphadenopathy of at least 6 months duration and affecting two or more extrainguinial sites in the absence of an illness or drug use known to cause lymphadenopathy. "Immunological Diseases", supra., at p.445–446.

AIDS and its related syndromes are attributed to a lymphocytotrophic retrovirus designated: human immunodeficiency virus (HIV). HIV can be readily recovered from individuals with early stages of AIDS but cannot always be recovered intact from individuals in the late stages of AIDS. It is postulated that this is because the subset of T cells thought to harbor the virus has been depleted.

Serological screening techniques are being utilized worldwide for the detection of human immunodeficiency virus type 1 (HIV-1). The presence of antibody against human immunodeficiency virus type 1 (HIV-1) is considered a strong indicator of HIV-1 infection. An ELISA assay is currently being utilized on serum samples in most hospitals and screening rooms to make this determination. A similar assay is being used to detect the presence of simian immunodeficiency virus.(SIV), a virus similar to HIV found in nonhuman primates. If the serum sample is positive, an aliquot of the sample is screened by a Western blot assay kit for confirmation. The presence of antibody against two to three of the major protein bands of the virus is considered a positive confirmation and identification that the serum sample donor is infected.

Experimental results indicate that the currently used ELISA assays do not detect all HIV infected individuals. This is because some HIV infected individuals do not have detectable levels of serum antibody to HIV-1 and current techniques do not identify individuals who lack detectable levels of HIV-1 antibodies. Studies indicate that there can be a considerable time lag between detection of HIV-1 infection and seroconversion. Additionally, some HIV infected but seronegative individuals might never convert but will remain infected throughout their lives. Thus, there is a significant number of false negatives being reported. The existence of HIV-1 infected but seronegative individuals has been documented using the polymerase chain reaction (PCR) technique, virus isolation techniques, and in situ hybridization. Identifying infected but seronegative individuals is critical to controlling the spread of the disease due to its highly contagious nature. Additionally, data from such assays have important consequences for the clinical management, follow-up, and therapy of infected individuals as well as maintaining the safety of health care workers who come into contact with infected individuals.

Recently a method for detecting HIV infection in seronegative individuals was reported in the scientific literature. (Jehuda-Cohen, T., "Polyclonal B-cell activation reveals antibodies against human immunodeficiency virus type 1 (HIV-1) in HIV-1-seronegative individuals", *Proc. Nat. Acad. Sci. USA,* Vol 87, pp.3972–3076, 1990). In this article, a method is described wherein peripheral blood mononuclear cells (PBMC) are isolated from the blood and then exposed to a mitogen such as pokeweed mitogen. It was found that in those patients which had been infected by HIV and were seronegative, incubation of isolated PBMC with pokeweed mitogen caused the PBMC to secrete immunoglobulins that were specific for HIV. Thus, this test provides the possibility of identifying a significant portion of those patients that have been infected with HIV but are seronegative.

However, there are some serious problems in using this test in the clinic. First of all, the blood from the patient who has been exposed to HIV has to be collected and then fractionated to isolate the peripheral blood mononuclear cells. These cells then must be suspended in a growth medium with a mitogen therein and incubated for an appropriate amount of time. These procedures must be conducted under sterile conditions. The supernatant is then tested for the presence of HIV specific antibody. The process of maintaining a sterile environment is time-consuming and the process of isolating and collecting PBMC exposes the technician to blood that contains HIV. While this practice may be acceptable in the research laboratory, in the clinical laboratory, where hundreds, and in some cases thousands of blood samples are handled each week, the possibility of a technician becoming infected by the blood is greatly increased.

What is needed in the art is an assay which allows detection of infection by a particular antigen, such as the HIV virus, prior to seroconversion. The assay should include minimal exposure to the blood by the technician and, at the same time, provide a safe, easy and inexpensive method of screening large numbers of blood samples for viral infection.

SUMMARY OF THE INVENTION

The present invention relates to an improved assay for detecting antibodies in whole blood of individuals who test seronegative by conventional assay techniques, thus aiding in the diagnosis of possible retrovirus infections. More particularly, the present invention relates to an improved assay and kit which utilizes a mitogen, such as pokeweed mitogen, in whole blood to stimulate the production of antibodies previously undetectable.

In accordance with the present invention, a blood sample is drawn into a test tube, such as a vacutube, containing an effective concentration of a solution of a mitogen, such as pokeweed mitogen. The blood sample to be tested is cultured in vitro in the presence of the pokeweed mitogen. Other activators of human B cells may be used in place of or in addition to the pokeweed mitogen to achieve the same function. After incubation, an aliquot is taken from the top of the fluid and is then assayed for the presence of desired antibodies using standard ELISA procedures and/or Western Blot analysis. If the sample is to be assayed at a later date, the blood may be centrifuged and the supernatant fluid may be collected, frozen and stored. Results may be verified utilizing the technique of polymerase chain reaction (PCR).

Alternatively, PBMC's may be separated from the blood sample to be tested and cultured alone with a mitogen, such as pokeweed mitogen, and in a culture medium. PBMC alone may be used to detect "hidden" antibodies to cancer epitopes or for matching donors for transplantations.

Accordingly, it is an object of the present invention to provide a simple and sensitive assay for the detection of retrovirus infections in patients who are infected but are seronegative for the virus.

It is another object of the present invention to provide a simple and sensitive assay to be used for predicting the possibility of organ or tissue rejection due to recall stimulation of antibody production in transplant recipients.

It is another object of the present invention to provide a method and kit for early detection of some forms of cancer.

It is another object of the present invention to provide a method for diagnosing HIV infection.

It is another object of the present invention to provide an assay kit which is self contained and does not require the separation of peripheral blood mononuclear cells prior to assay.

It is another object of the present invention to provided an assay and assay kit for diagnosis of retrovirus infections which decreases risk to the health care workers by simplifying the assay procedure, reducing the handling of the donor sample, and thereby reducing the risk of infection.

It is another object of the present invention to provide a means for detecting antibodies when levels of antibodies in the blood are lower than those currently detectable by conventional assay systems.

These and other objects, features and advantages of the present invention will become apparent after a review of the following detailed description of the disclosed embodiment and the appended claims.

DETAILED DESCRIPTION OF THE PRESENT INVENTION

The present invention comprises a method and kit for the detection of "hidden" antibodies in whole blood in individuals who tested seronegative by conventional assay techniques. Additionally, the invention comprises a method for detecting HIV antibodies in whole blood of those individuals who have been infected with HIV but appear seronegative with conventional assay techniques. The method involves incubating whole blood of seronegative individuals in the presence of a mitogen, such as pokeweed. The mitogen causes activation of the peripheral blood mononuclear cells and the production of antibodies. The presence of specific antibodies may then be determined by the use of any conventional assay techniques such as those outlined above.

In the present invention, any mitogen can be used to activate the cells. The mitogen can be either T-cell dependent or T-cell independent. The preferred mitogen is pokeweed mitogen. Other mitogens can be used in practicing the present invention and include, but are not limited to, lectins, such as, concanavalin A; bacterial endotoxins; bacterially derived lipid A; a variety of viruses; and, biological agents such as lymphokines, including, but not limited to, interleukin-4, interleukin-5 and interleukin-6, or other anti-immunoglobulin reagents. The optimal concentration of mitogen is easily determined without undue experimentation by one of ordinary skill in the art. With regard to the preferred mitogen, pokeweed mitogen, the preferred concentration range is between approximately 1:100 and 1:1600 dilutions of stock PWM. The most preferred concentration range is between approximately 1:200 and 1:1:400 dilutions of stock PWM. The preferred source of the stock PWM is GIBCO, New York, N.Y. The lyophilized PWM is reconstituted with 5 ml of distilled water to make the stock solution.

Culture medium means any medium that can be used to practice the present invention, including but not limited to RPMI 1640 (GIBCO, New York, N.Y.), preferably supplemented with appropriate antibiotics and glutamine. Other culture media which may be used in practicing the present invention include, but are not limited to, Eagles, Dulbecco's, McCoy's, Media 199 and Waymouth's media.

The present invention also includes a kit comprising a blood collection container containing an effective concentration of mitogen therein. The container can optionally contain a culture medium. The preferred container is a test tube. The blood collection container can be plastic, glass, or any other material that is compatible with culturing blood. It is to be understood that the present invention also includes blood containing means other then a blood collection tube including, but not limited to, microtiter plates containing wells in which the blood can be incubated, tissue culture flasks, glass flasks such as an erlenmeyer flask, and any other container in which the blood can be cultured The method of the present invention includes optionally separating the blood cells from the fluid portion of the blood so that the presence of antibodies can be determined. The separation of the blood cells from the fluid portion of the blood can be done by any of several methods well known to those of ordinary skill in the art, including centrifugation or filtration. It is to be understood, that the blood cells do not need to be physically separated from the fluid. Although, in those situations where risk of infection is low, PBMC's may be separated from the blood prior to culture and assay. After incubation of the whole blood with the mitogen, fluid from the top of the blood can easily be extracted and tested for antibody. Optionally, the red blood cells can be lysed either by mild osmotic shock or with a mild detergent. In this way, the white blood cells remain viable.

In one embodiment of the present invention, whole blood is collected in a blood collection tube containing culture medium and mitogen. The blood samples are then incubated with an approximately 1:500 final dilution of pokeweed mitogen at a concentration of $2\times10^6$ viable cells per ml for four days at 37° C. in a 7% $CO_2$ humidified atmosphere. The blood is then centrifuged and the supernatant fluid is collected and assayed within approximately 24 hours for reactive antibodies by ELISA and/or Western blot techniques. In the alternative, an aliquot of fluid may be taken directly from the sample. Each sample should be screened for antibody by ELISA first, samples considered positive may then be subjected to Western blot analysis.

It is to be understood that the present invention can be used to detect antibodies in a wide variety of conditions, including, but not limited to, antibodies to foreign antigens involved in transplantation of organs and tissues. Supernatants of the blood from a potential recipient can be prepared and treated according to the present invention and then stored so that when a potential donor is found, the PBMC from the donor is mixed with the supernatant fluid from the recipient. The presence and level of antibodies that bind to the donor's cells can be measured by a variety of different means including but not limited to lysis by complement or by differential staining and FACS analysis. These methods of detecting antibodies are well known to those of ordinary skill in the art.

The present invention can be used to determine if "hidden" antibodies are present after or during infection by a microorganism including, but not limited to, yeasts, bacteria, viruses, protozoa, and other classes of microorganisms.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Blood from 10 different patients was analyzed for the presence of HIV specific antibodies. In this example, the blood was collected from the patients, and PBMC were isolated from the blood. For each patient, whole blood and the PBMC were incubated in a medium containing pokeweed mitogen. For whole blood, 0.4 ml of whole blood was mixed with 2 mls of culture medium. The medium was a 1:500 final dilution of PWM in RPMI 1640 supplemented with penicillin (100 units per ml), streptomycin (100 µg/ml), 2 mM L-glutamine, and 10% (v/v heat-inactivated (56° C., 30 min) fetal calf serum (all from GIBCO). For PBMC, the cells were incubated in the same medium at a concentration of $2\times10^6$ cells per ml. In addition, serum from each patient was analyzed for the presence of HIV antibodies. The cultures of whole blood and PBMC were performed in triplicate in sterile test tubes and incubated for 4 days at 37° C. in a 7% $CO_2$ humidified atmosphere. The cultures were then centrifuged, and the supernatant fluid was collected and assayed within 24 hours for HIV-1-reactive antibodies.by ELISA and PCR tests. The ELISA tests used were purchased from Abbott Laboratories. The results are as follows:

| Patient | Blood | PBMC | Serum | PCR |
|---|---|---|---|---|
| 1 | − | − | − | − |
| 2 | − | − | − | − |
| 3 | − | − | − | − |
| 4 | − | − | − | − |
| 5 | 1.2–1.5* | 1.2–1.4* | − | + |
| 6 | − | − | − | − |
| 7 | − | − | − | − |
| 8 | − | − | − | − |
| 9 | + | + | + | + |
| 10 | + | + | + | + |

*O.D. reading that is "low positive" in a seronegative patient that proved to be positive by PCR. Thus, whole blood was just as good as PBMC for detecting HIV-reactive antibodies after incubation with pokeweed mitogen.

EXAMPLE II

Blood from four different monkeys was analyzed for the presence of SIV specific antibodies. In this example, the blood was collected from the monkeys, and PBMC were isolated from the blood. The plasma from each sample was collected for serology after centrifugation. For each monkey, whole blood and the PBMC were incubated in a medium containing pokeweed mitogen. For whole blood, 0.4 ml of whole blood was mixed with 2 mls of culture medium. The mediun was a 1:500 final dilution of PWM in RPMI 1640 supplemented with penicillin (100 units per ml), streptomycin (100 μg/ml), 2 mM L-glutamine, and 10% (v/v heat-inactivated (56° C., 30 min) fetal calf serum (all from GIBCO). For PBMC, the cells were incubated in the same medium at a concentration of $2\times10^6$ cells per ml. In addition, serum from each monkey was analyzed for the presence of SIV antibodies. The cultures of whole blood and PBMC were performed in triplicate in sterile test tubes and incubated for 4 days at 37° C. in a 7% $CO_2$ humidified atmosphere. The cultures were then centrifuged, and the supernatant fluid was collected and assayed within 24 hours for SIV-1-reactive antibodies.by ELISA and Western Blot tests. The results are as follows:

| Monkey | Serum | PBMC | Whole Blood |
|---|---|---|---|
| Mangaby | + | 0.521 (++) | 0.869 (++) |
| Mangaby | − | 0.211 (+) | 0.351 (+) |
| Rhesus | + | 0.469 (++) | 0.1208 (++) |
| Rhesus | − | 0.157 (−) | 0.208 (−) |

EXAMPLE III

Blood from eight different monkeys was analyzed for the presence of SIV specific antibodies. In this example, the blood was collected from the monkeys, and PBMC were isolated from the blood. The plasma from each sample was collected for serology after centrifugation. For each monkey, whole blood and the PBMC were incubated in a medium containing pokeweed mitogen. For whole blood, 0.4 ml of whole blood was mixed with 2 mls of culture medium. The medium was a 1:500 final dilution of PWM in RPMI 1640 supplemented with penicillin (100 units per ml), streptomycin (100 μg/ml), 2 mM L-glutamine, and 10% (v/v heat-inactivated (56° C., 30 min) fetal calf serum (all from GIBCO). For PBMC, the cells were incubated in the same medium at a concentration of $2\times10^6$ cells per ml. In addition, serum from each monkey was analyzed for the presence of SIV antibodies. The cultures of whole blood and PBMC were performed in triplicate in sterile test tubes and incubated for 4 days at 37° C. in a 7% $CO_2$ humidified atmosphere. The cultures were then centrifuged, and the supernatant fluid was collected and assayed within 24 hours for SIV-1-reactive antibodies.by ELISA and Western Blot tests. The results are as follows:

| | O.D. at 405 mm | | |
|---|---|---|---|
| Animal | Blood | PBMC | Serum |
| G | 1.059 | 0.0620 | +low |
| H | 0.390 | 0.110 | − |
| 200 | 0.869 | 0.468 | +low |
| 315 | 0.939 | 0.491 | +low |
| 2h | 0.585 | 0.146 | − |
| PBi | 1.481 | 0.867 | +low |
| neg. control | 0.407 ± 0.070 | 0.120 ± 0.014 | +low |
| cut-off | 0.547 | 0.148 | |

Note that the O.D. of whole blood is higher then in PBMC, but so is the negative control. Therefore the cutoff value should be subtracted from the actual reading.

EXAMPLE IV

Blood from eight different monkeys was analyzed for the presence of SIV specific antibodies. In this example, the blood was collected from the monkeys, and PBMC were isolated from the blood. The plasma from each sample was collected for serology after centrifugation. For each monkey, whole blood and the PBMC were incubated in a medium containing pokeweed mitogen. For whole blood, 0.4 ml of whole blood was mixed with 2 mls of culture medium. The medium was a 1:500 final dilution of PWM in RPMI 1640 supplemented with penicillin (100 units per ml), streptomycin (100 μg/ml), 2 mM L-glutamine, and 10% (v/v heat-inactivated (56° C., 30 min) fetal calf serum (all from GIBCO). For PBMC, the cells were incubated in the same medium at a concentration of $2\times10^6$ cells per ml. In addition, serum from each monkey was analyzed for the presence of SIV antibodies. The cultures of whole blood and PBMC were performed in triplicate in sterile test tubes and incubated for 4 days at 37° C. in a 7% $CO_2$ humidified atmosphere. The cultures are then centrifuged, and the supernatant fluid was collected and assayed within 24 hours for SIV-1-reactive antibodies.by ELISA and Western Blot tests. The results are as follows:

| Animal | PBMC | Blood |
|--------|------|-------|
| 1 | + | + |
| 2 | + | + |
| 3 | + | +/− |
| 4 | + | + |
| 5 | − | N.D. |
| 6 | − | − |
| 7 | − | − |
| 8 | + | N.D. |

As can be seen from the data, there is excellent correlatio between PBMC and whole blood.

It should be understood, of course, that the foregoing related only to a preferred embodiment of the present invention and that numerous modifications or alterations may be made therein without departing from the spirit and the scope of the invention as set forth in the appended claims.

I claim:

1. A method for the detection of antibodies directed against a retrovirus in a sample comprising the following steps:
   a) obtaining a whole blood sample;
   b) incubating the whole blood sample in a culture in the presence of a media containing a mitogen to induce polyclonal activation of peripheral blood mononuclear cells and the expression of retroviral specific antibodies;
   c) exposing the resultant culture of step b) to a retroviral antigen, thereby allowing an antigen-antibody immune complex to form; and
   d) detecting the antigen-antibody immune complex of step c);
   thereby detecting the presence of retroviral specific antibodies.

2. The method of claim 1, wherein the culture of step b) results in a supernatant, and the supernatant is exposed to a retroviral antigen, thereby allowing an antigen-antibody immune complex to form.

3. The method of claim 1, wherein the mitogen is pokeweed mitogen, lectins, bacterial endotoxins, a viruse, lipid A or lymphokines.

4. The method of claim 1, wherein the mitogen is pokeweed mitogen.

5. A kit for the detection of antibodies directed against a retrovirus from a subject, comprising: a container for collecting whole blood samples, wherein the container contains a media containing a mitogen, effective to induce polyclonal activation of peripheral blood mononuclear cells and the expression of retroviral specific antibodies of the whole blood sample.

6. The kit of claim 5, wherein the kit additionally comprises an assay for the detection of retroviral specific antibodies.

7. The kit of claim 6, wherein the assay is an enzyme linked immunosorbent assay, a western blot, or an immunofluorescence assay.

8. The method of claim 1, wherein the mitogen is pokeweed mitogen, lectins, bacterial endotoxins, viruses, lipid A or lymphokines.

9. The method of claim 1, wherein the mitogen is pokeweed mitogen.

10. The kit of claim 5, wherein the container is made of a plastic, glass, or metal material.

11. The kit of claim 5, wherein the container is a test tube or a flask.

12. The kit of claim 5, wherein the container is vacuum sealed.

13. The kit of claim 5, wherein the container is a vacutube.

14. The method of claim 1, wherein the mitogen activates B-lymphocytic cells.

* * * * *